(12) United States Patent
Silvestri

(10) Patent No.: US 12,208,061 B2
(45) Date of Patent: Jan. 28, 2025

(54) STERILE AZTREONAM PACKAGE

(71) Applicant: EXORAO LIFE SCIENCE S.R.L., Milan (IT)

(72) Inventor: Maurizio Silvestri, Genzano di Roma (IT)

(73) Assignee: EXORAO LIFE SCIENCE S.R.L., Milan (IT)

( * ) Notice: Subject to any disclaimer, the term of this patent is extended or adjusted under 35 U.S.C. 154(b) by 633 days.

(21) Appl. No.: 17/433,769

(22) PCT Filed: Feb. 24, 2020

(86) PCT No.: PCT/IB2020/051549
§ 371 (c)(1),
(2) Date: Aug. 25, 2021

(87) PCT Pub. No.: WO2020/174365
PCT Pub. Date: Sep. 3, 2020

(65) Prior Publication Data
US 2022/0142866 A1    May 12, 2022

Related U.S. Application Data

(60) Provisional application No. 62/811,872, filed on Feb. 28, 2019.

(51) Int. Cl.
| A61J 1/14 | (2023.01) |
| A61J 1/20 | (2006.01) |
| A61K 9/00 | (2006.01) |
| A61K 9/14 | (2006.01) |
| A61K 31/427 | (2006.01) |
| A61K 47/18 | (2017.01) |

(52) U.S. Cl.
CPC ......... *A61J 1/2093* (2013.01); *A61J 1/1406* (2013.01); *A61J 1/2027* (2015.05); *A61K 9/0019* (2013.01); *A61K 9/145* (2013.01); *A61K 31/427* (2013.01); *A61K 47/183* (2013.01)

(58) Field of Classification Search
None
See application file for complete search history.

(56) References Cited

U.S. PATENT DOCUMENTS

| 2003/0055034 A1* | 3/2003 | Montgomery ....... A61K 9/0075 424/46 |
| 2004/0062721 A1* | 4/2004 | Montgomery ....... A61K 9/0075 424/46 |
| 2006/0093765 A1* | 5/2006 | Mueller .................. B29C 65/76 428/35.2 |

FOREIGN PATENT DOCUMENTS

CN          102727490 A  * 10/2012

* cited by examiner

*Primary Examiner* — Susan S Su
*Assistant Examiner* — Katherine-Ph Minh Pham
(74) *Attorney, Agent, or Firm* — Olson & Cepuritis, Ltd.

(57) ABSTRACT

Enhanced stability for aztreonam is achieved by separate packaging of aztreonam and a physiologically acceptable liquid carrier therefor prior to constitution of an aztreonam solution suitable for administration by injection or inhalation. A manually activatable package having a chamber preferably containing anhydrous β-aztreonam powder and a separate chamber in the same package containing a solvent for the β-aztreonam powder for convenient constitution of β-aztreonam prior to administration is described.

7 Claims, 2 Drawing Sheets

STERILE AZTREONAM PACKAGE

CROSS-REFERENCE TO RELATED APPLICATIONS

This application is a U.S. National Stage of PCT/IB2020/051549, filed Feb. 24, 2020, which claims priority to U.S. Application No. 62/811,872, filed Feb. 28, 2019, each of which is incorporated herein by reference.

FIELD OF INVENTION

This invention relates to sterile packaging of antibiotics. More particularly, this invention relates to convenient sterile packaging of aztreonam for administration by injection or inhalation.

BACKGROUND OF INVENTION

Aztreonam ($C_{13}H_{17}N_5O_8S_2$) is a monocyclic beta lactam antibiotic active against gram-negative bacteria. Aztreonam exhibits potent and specific activity in vitro against a wide spectrum of gram-negative aerobic pathogens including *Pseudomonas aeruginosa*. It has no useful activity against gram-positive bacteria or anaerobes, but has very broad spectrum against gram-negative aerobes, including *Pseudomonas aeruginosa*. Aztreonam, unlike the majority of beta-lactam antibiotics, does not induce beta-lactamase activity and its molecular structure confers a relatively high degree of resistance to hydrolysis by beta-lactamases (such as penicillinases and cephalosporinases) produced by most gram-negative and gram-positive pathogens. Aztreonam, therefore, is usually active against gram-negative aerobic microorganisms that are resistant to antibiotics hydrolyzed by beta-lactamases. It is active against many strains that are multiply-resistant to other antibiotics, such as certain cephalosporins, penicillin, and aminoglycosides. Aztreonam maintains its antimicrobial activity over a pH range of 6 to 8 in vitro, as well as in the presence of human serum and under anaerobic conditions.

Aztreonam is poorly absorbed when administered orally, however, and usually is administered in a solubilized form by intravenous, intramuscular, intraperitoneal injection, or by inhalation as a dry powder with the assistance of a nebulizer, to treat infections of the lungs, bones, skin, and soft tissues caused by Gram-negative pathogens. The bactericidal action of aztreonam results from the inhibition of bacterial cell wall synthesis due to a high affinity of aztreonam for penicillin binding protein 3 (PBP3). By binding to PBP3, aztreonam inhibits the third and last stage of bacterial cell wall synthesis. Cell lysis is then mediated by bacterial cell wall autolytic enzymes such as autolysins. Aztreonam is believed to interfere with an autolysin inhibitor.

The solubilized form of aztreonam is relatively unstable, however, is stored frozen, and has a limited shelf-life. According to product literature, reconstituted solubilized aztreonam solutions for intravenous infusion should be used within 48 hours if kept at controlled room temperature or within seven days if refrigerated at 2° C. to 8° C.

Constitution of the injectable solution is accomplished by the addition of an appropriate diluent, such as water-for-injection, or an infusion solution. The infusion solution can be Sodium Chloride Injection, USP, 0.9%; Ringer's Injection, USP; Lactated Ringer's Injection, USP; Dextrose Injection, USP (5% or 10%); and the like. The constitution step, however, represents a substantial risk factor for contamination. Severe infections can be transmitted to the receiving patient if an aseptic procedure is not followed.

The present invention minimizes the likelihood of contamination by providing in a single, aseptic package a stabilized medicament together with a diluent suitable for reconstitution of an injectable dose.

SUMMARY OF INVENTION

Stability of aztreonam is enhanced by packaging sterile, solid β-aztreonam separately from a solvent and carrier therefor. The packaging facilitates a convenient and efficient preparation of an aztreonam solution shortly before administration while preserving sterility and avoiding contamination.

A convenient, manually activatable constituting package for aztreonam has a solids chamber which contains sterile, anhydrous aztreonam powder with or without solid excipients and a liquid chamber which contains a physiologically compatible aqueous solvent and liquid excipients for aztreonam. The chambers are separated by a partition therebetween to prevent inadvertent premature mixing of chamber contents. The partition can be manually breached when the contents of the solids chamber is to be combined with the contents of the liquid chamber prior to administration of the aztreonam to a patient suspected of suffering from gram-negative bacterial infection. Sterility of aztreonam is preserved up to the time of administration.

DESCRIPTION OF PREFERRED EMBODIMENTS

Figure 1:
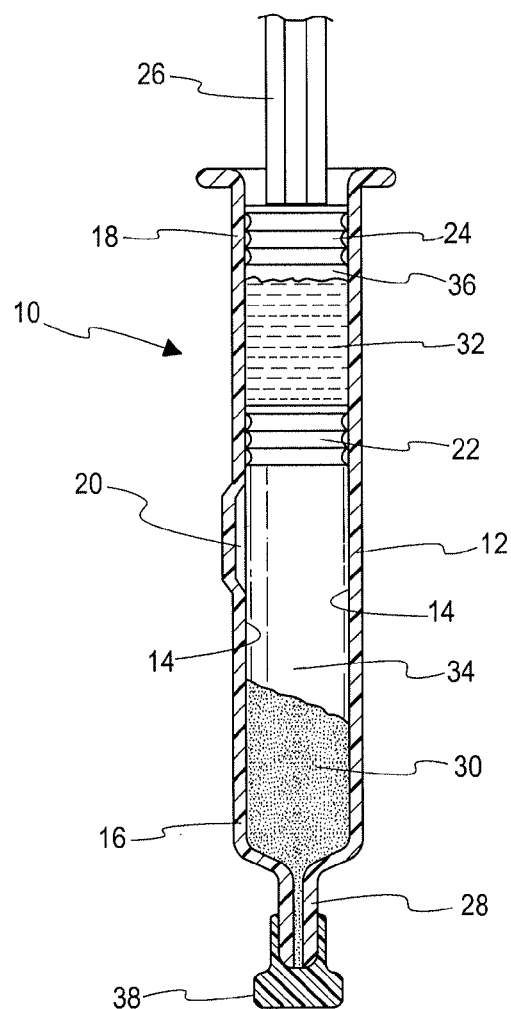
FIG. 1 is a side elevation view of a dual chamber syringe illustrating an embodiment of the present invention.

Aztreonam has the chemical name (Z)-2-[[[(2-amino-4-thiazolyl)[[(2S,3S)-2-methyl-4-oxo-1-sulfo-3-azetidinyl]carbamoyl]methylene]amino]oxy]-2-methylpropionic acid, has the structural formula

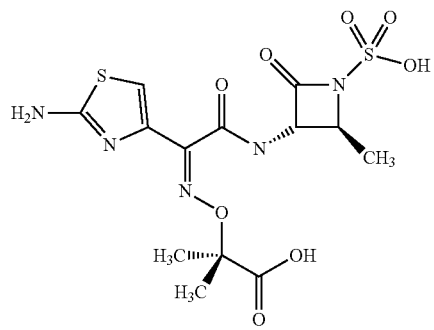

and a molar mass of 435.433 g/mol.

Aztreonam is known to exist in several polymorphic forms, including the alpha (α), beta (β), delta (δ) and gamma (γ) crystal forms, which are suitable for practicing the present invention. Among these polymorphic forms the j-form is anhydrous, substantially non-hygroscopic, and more stable.

The β-form of aztreonam is preferred for constitution as an injectable solution, or for inhalation, and is packaged in a manually activatable, dual chamber package having a solids chamber (a first chamber) and a liquid chamber (a second chamber).

Preferably, the packaging, i.e., a dual-chamber syringe, a dual chamber pouch, and the like, provides an oxygen barrier to the contents within and also a pH protective interior coating.

A first or solids chamber can contain only sterile β-aztreonam powder, or β-aztreonam powder together with solid solubilizing and stabilizing excipients. A bulking agent such as a disaccharide, e.g., sucrose, lactose, trehalose, and the like may be present as well. A second or liquid chamber can contain a physiologically acceptable carrier for β-aztreonam. The carrier can be sterile water, an aqueous solution of one or more of the aforementioned excipients, an aqueous solution of an organic or inorganic acid that can form a pharmacologically compatible base addition salt with β-aztreonam, or a water-soluble organic solvent or cosolvent such as propylene glycol, glycerin, polyethylene glycol 300, polyethylene glycol 400, and the like, and mixtures thereof. If the injectable formulation is an organic formulation, a surfactant such as pegylated castor oil (Cremophor EL) or a hydrogenated castor oil with varying amounts of ethylene oxide can be present as well.

An additional organic or inorganic acid can also be added to the constituted β-aztreonam solution, if desired, to adjust or stabilize the final pH of the injectable or inhalable product.

The carrier solution, if aqueous at least in part, can also contain a buffer, preferably a phosphate buffer, for enhancing β-aztreonam solubility and for maintaining the constituted solution at a pH value in the range of about 4.5 to about 7.5, preferably about 5.5 to about 7.5, so as to assure complete dissolution of β-aztreonam present over the anticipated product temperature range.

Suitable organic acids are oxalic acid, maleic acid, acetic acid, succinic acid, citric acid, and the like, as well as the basic amino acids such as arginine, lysine, histidine, and mixtures thereof, e.g., a mixture of L-arginine and L-lysine, a mixture of L-arginine and L-histidine, and a mixture of L-lysine and L-histidine.

Suitable inorganic acids are hydrochloric acid, phosphoric acid, nitric acid, sulphuric acid, and the like.

If the aqueous solution present in the liquid chamber contains a basic amino acid, the aqueous solution can also contain an amount of the corresponding basic amino acid hydrochloride, e.g., arginine hydrochloride, lysine hydrochloride, histidine hydrochloride, to gain a "salting in" effect and further enhance solubility.

A suitable phosphate buffer consists of a mixture of monobasic potassium phosphate and dibasic sodium phosphate, and the like.

In another embodiment of the invention the solids chamber can contain not only the β-aztreonam powder but also the aforementioned solid excipients in dry powder form, and the liquid chamber contains only solvent in an amount sufficient to dissolve the compounds present in the solids chamber.

Referring to the drawings, FIG. 1 illustrates a dual chamber mixing syringe embodiment in which syringe 10 is provided with a hollow syringe body 12 having inner wall 14, distal discharge end portion 16, and proximal piston rod receiving end portion 18. Inner wall 14 defines a bypass region, such as groove 20, at a midportion of hollow syringe body 12.

First piston 22 in hollow syringe body 12 together with distal discharge end portion 16 defines a first chamber 34 which also includes the bypass region. Discharge end portion terminates in a dispensing nozzle 28 which can have a male Luer configuration adapted to receive a female Luer fitting of a cannula. Dispensing nozzle 28 is shown fitted with sealing cap 38.

Second piston 24 is situated in hollow syringe body 12 in proximal piston rod receiving end portion 18 and together with first piston 22 defines a second chamber 36.

First chamber 34 is the solids chamber and contains sterile, anhydrous β-aztreonam either alone or together with the aforesaid optional constituents in dry powder form. Second chamber 36 is the liquid chamber and contains solvent 32 for the solids 30 in first chamber 34. The solvent can be a saline solution or sterile water suitable for injection. The solvent can also include a water-soluble, physiologically compatible organic solvent or cosolvent for β-aztreonam. A β-lactamase inhibitor, e.g., avibactam, can be included as well, if desired.

The solvent can also be a solution in water of one or more of the optional solid constituents or excipients discussed hereinabove. In either case, the active ingredient, β-aztreonam, is maintained as an anhydrous powder until such time when second piston 24 is urged axially toward first piston 22 by depressing piston rod 26 and moves first piston 22 past groove 20, thereby introducing physiologically compatible solvent 32 into first chamber 34 and combining solvent 32 with β-aztreonam powder 30 in first chamber 34. Dissolution of powder 30 is achieved by shaking the syringe after the solvent has been combined with the β-aztreonam until a clear solution can be seen in the first chamber. The clear solution produced in the foregoing manner is then ready to be dispensed via dispensing nozzle 28 by continued movement of pistons 22 and 24 toward dispensing nozzle 28.

Pistons 22 and 24 must, of course, be compatible with the pH range of chamber contents before as well as after constitution of the β-aztreonam solution.

Figure 2:
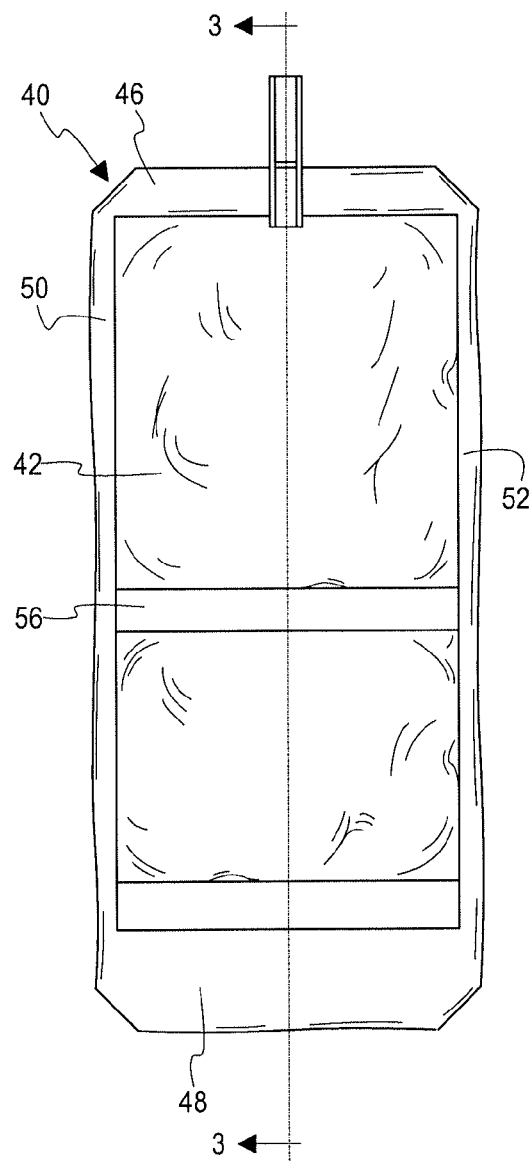
FIG. 2 is a plan view of a dual chamber pouch illustrating another embodiment of the present invention.
Figure 3:
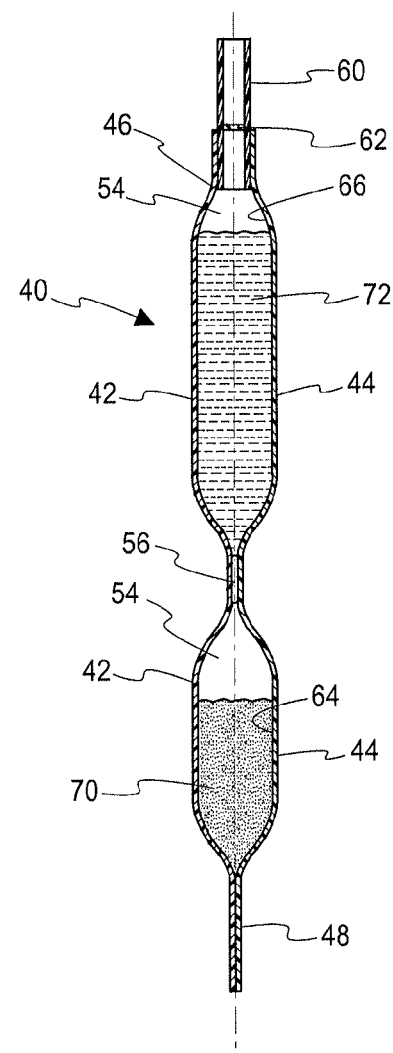
FIG. 3 is a sectional view of the dual chamber pouch of FIG. 2 taken along plane 3-3.

FIGS. 2 and 3 illustrate a second embodiment which utilizes a two-chamber flexible pouch 40 having front sheet 42 and back sheet 44 arranged in opposing face-to-face relationship relative to one another and joined together along a top edge 46, a bottom edge 48, first side edge 50 and second side edge 52 to define a sealed pouch with an interior space 54. Frangible seal 56 partitions interior space 54 into first chamber 64 and second chamber 66. First chamber 64 serves as the solids chamber and second chamber 66 serves as the liquid chamber which contains a solvent for the solids in first chamber 64. Second chamber 66 is provided with dispensing nozzle 60 sealed by pierceable sealing membrane 62. Components 70 of first chamber 64 can be the same as those discussed hereinabove for first chamber 34 in hollow syringe body 12. Likewise, the contents 72 of second chamber 66 can be the same as those discussed hereinabove for second chamber 36 in hollow syringe body 12.

To combine the contents of both chambers prior to use, frangible seal 56 is breached by urging the liquid in second chamber 66 against frangible seal 56.

Preferred material of construction for pouch 40 is a thermoplastic film or sheet such as polyethylene film or sheet, polyvinylchloride film or sheet, ethylenevinyl acetate film or sheet, PL2040 plastic sheet, and the like material compatible with the contents of the pouch.

Table A, below, sets forth preferred sterile β-aztreonam packages that embody the invention.

TABLE A

Preferred Sterile β-Aztreonam Packages

| | | | Chamber | | | | | | | | |
|---|---|---|---|---|---|---|---|---|---|---|---|
| | 1 (solids) | | 2 (liquid) | | | | | | | Volume, ml | |
| Example Number | Sterile β-Aztreonam | Dual Chamber Device | WFI q.s. to ml | L-Arginine, mg | L-Lysine, mg | Na3 PO4, mg | Na2HPO4, mg | NaH2PO4, mg | Preferred Administration Route | Chamber 1 | Chamber 2 |
| 1 | 75 mg | Syringe | 3 | — | 53 | — | — | — | Inhalation | 5 | 3 |
| 2 | 500 mg | Syringe | 3 | 421 | — | — | — | — | I.M.-I.V. | 5 | 3 |
| 3 | 1.0 g | Syringe | 3 | 211 | 529 | — | — | 140 | I.M.-I.V. | 5 | 3 |
| 4 | 1.0 g | Syringe | 3 | — | 705 | — | — | 70 | I.M.-I.V. | 5 | 3 |
| 5 | 1.0 g | Pouch | 50 | 780 | — | — | — | 140 | I.V. | 12 | 50 |
| 6 | 2.0 g | Syringe | 8 | 780 | 671 | — | — | 280 | I.M.-I.V. | 12 | 8 |
| 7 | 2.0 g | Syringe | 3 | — | 1410 | — | — | 140 | I.M.-I.V. | 12 | 3 |
| 8 | 2.0 g | Pouch | 50 | 1560 | — | — | — | 280 | I.V. | 12 | 50 |
| 9 | 1.0 g | Syringe | 5 | — | — | 380 | — | — | I.M.-I.V. | 5 | 6 |
| 10 | 2.0 g | Syringe | 10 | — | 1410 | — | 10 | 10 | I.M.-I.V. | 12 | 10 |

NOTES

Sterile β-aztreonam is the preferred crystalline form but other sterile polymorphic forms (i.e., α, γ, δ) can be used Phosphate buffers may be substituted with other organic or inorganic buffers Arginine and Lysine ratios can be modified to optimize solubility profile Phosphate buffer ratios can be modified to achieve desired pH interval WFI = sterile water for injection

Example 11: Stability of Constituted Solutions of Aztreonam

Stability of β-aztreonam solutions containing 1-arginine or 1-lysine and constituted with sterile water-for-injection was evaluated by storing the constituted solutions in a 30 milliliter glass vial at 25° C. for 48 hours. The stored solutions were sampled at zero, 3, 6, 12, 24, 36 and 48 hours storage. The evaluated solutions are listed in Table B, below.

TABLE B

Constituted Solutions

| Solutions | β-Aztreonam (AZT) (mg) | L-Arginine (mg) | L-Lysine (mg) | Water (mL) |
|---|---|---|---|---|
| AZT 2G + ARG + 50 mL | 2000 | 1600 | — | 50 |
| AZT 1G + ARG + 50 mL | 1000 | 800 | — | 50 |
| AZT 2G + LYS + 50 mL | 2000 | — | 1344 | 50 |
| AZT 1G + LYS + 50 mL | 1000 | — | 672 | 50 |
| AZT 1G + LYS + 3 mL | 1000 | — | 672 | 3 |
| AZACTAM ®[1] 2G + 50 mL | 2000 | 1560 | — | 50 |
| AZACTAM ®[1] 1G + 50 mL | 1000 | 780 | — | 50 |
| AZACTAM ®[1] 1G + 3 mL | 1000 | 780 | — | 3 |

[1]AZACTAM ® is an intravenous aztreonam solution commercially available from Bristol-Myers Squibb, Princeton, NJ, USA. In addition to aztreonam the solution contains 700 mg Dextrose Hydrous, USP and 780 mg of arginine per one gram of aztreonam present.

The pH value of the stored solutions was determined using Mettler Toledo Five Easy pH meter with a combined electrode. The solutions were tested without dilution. The pH measurement results are reported in Table C, below.

TABLE C pH Measurements

| | Time of Measurement, hrs | | | | | |
|---|---|---|---|---|---|---|
| Solutions | t0 | t6 | t12 | t24 | t36 | t48 |
| AZT 1G + ARGsol 50 mL | 5.3 | 5.3 | 5.3 | 5.4 | 5.5 | 5.3 |
| AZT 1G + LYSsol 50 mL | 5.2 | 5.3 | 5.2 | 5.3 | 5.4 | 5.2 |
| AZACTAM ® 1G + 50 mL | 5.0 | 5.0 | 5.0 | 5.1 | 5.2 | 5.1 |
| AZT 2G + ARGsol 50 mL | 6.8 | 6.8 | 6.7 | 6.7 | 6.5 | 6.3 |
| AZT 2G + LYSsol 50 mL | 5.6 | 5.6 | 5.5 | 5.7 | 5.7 | 5.6 |
| AZACTAM ® 2G + 50 mL | 5.1 | 5.1 | 5.1 | 5.2 | 5.3 | 5.1 |
| AZT 1G + LYSsol 3 mL | 5.0 | 5.0 | 5.0 | 5.1 | 5.2 | 5.1 |
| AZACTAM ® 1G + 3 mL | 5.0 | 5.0 | 5.0 | 5.1 | 5.2 | 5.1 |

Degradation of aztreonam during storage was determined using a Waters Alliance HPLC system. Samples were diluted at appropriate concentrations in accordance with analytical method validation.

Detector: UV at 254 nm

Column Length: 100×4.6 mm

Stationary Phase: C18

Eluent: Phosphate Buffer, pH 3/Methanol 85/15

Flow Rate: 1 ml/min, isocratic @ room temperature

The noted aztreonam degradation results are reported in Table D, below.

TABLE D

Degradation of β-Aztreonam Solutions

| | % β-Aztreonam @ Time of Measurement (t) | | | | | |
|---|---|---|---|---|---|---|
| Solutions | t0 | t6 | t12 | t24 | t36 | t48 |
| AZT 1G + ARGsol 50 mL | 100 | 99.6 | 97.9 | 97.4 | 96.2 | 93.7 |
| AZT 1G + LYSsol 50 mL | 100 | 96.9 | 95.3 | 97.0 | 93.6 | 92.7 |
| AZACTAM ® 1G + 50 mL | 100 | 98.1 | 99.5 | 97.7 | 95.9 | 93.2 |
| AZT 2G + ARGsol 50 mL | 100 | 101.1 | 97.6 | 98.3 | 97.0 | 94.4 |
| AZT 2G + LYSsol 50 mL | 100 | 97.7 | 99.0 | 95.3 | 95.3 | 92.0 |

TABLE D-continued

Degradation of β-Aztreonam Solutions

| Solutions | % β-Aztreonam @ Time of Measurement (t) | | | | | |
|---|---|---|---|---|---|---|
| | t0 | t6 | t12 | t24 | t36 | t48 |
| AZACTAM ® 2G + 50 mL | 100 | 97.9 | 97.8 | 99.0 | 95.5 | 92.5 |
| AZT 1G + LYSsol 3 mL | 100 | 100.3 | 100.5 | 100.2 | 97.5 | 96 |
| AZACTAM ® 1G + 3 mL | 100 | 101.6 | 100.2 | 99.0 | 96.6 | 94.0 |

The foregoing data demonstrate the feasibility of separate compartment packaging of aztreonam powder and liquid excipients for constituting an injectable aztreonam composition.

The discussion above and the drawings are intended to be illustrative but not limiting. Still other variants within the spirit and scope of the present invention are possible and will readily present themselves to one skilled in the art.

The invention claimed is:

1. A two-chamber flexible pouch which comprises
front and back sheets arranged in opposing face-to-face relationship to one another, connected along a top edge, a bottom edge and opposite side edges to define a sealed pouch having an interior space;
a frangible seal disposed in the interior of the pouch between the front and back sheets and defining a first chamber and a second chamber;
β-aztreonam powder in the first chamber; and
a physiologically compatible solvent for the β-aztreonam powder in the second chamber.

2. The two-chamber pouch in accordance with claim 1 wherein the second chamber comprises a dispensing nozzle.

3. The two-chamber pouch in accordance with claim 1 wherein the first chamber contains only the β-aztreonam powder.

4. The two-chamber pouch in accordance with claim 1 wherein the first chamber contains the β-aztreonam powder together with excipients.

5. The two-chamber pouch in accordance with claim 1 wherein the physiologically compatible aqueous solvent is sterile water.

6. The two-chamber pouch in accordance with claim 1 wherein the physiologically compatible solvent is saline.

7. The two-chamber pouch in accordance with claim 1 wherein the physiologically compatible aqueous solvent is an aqueous solution of excipients.

* * * * *